Figure 1:
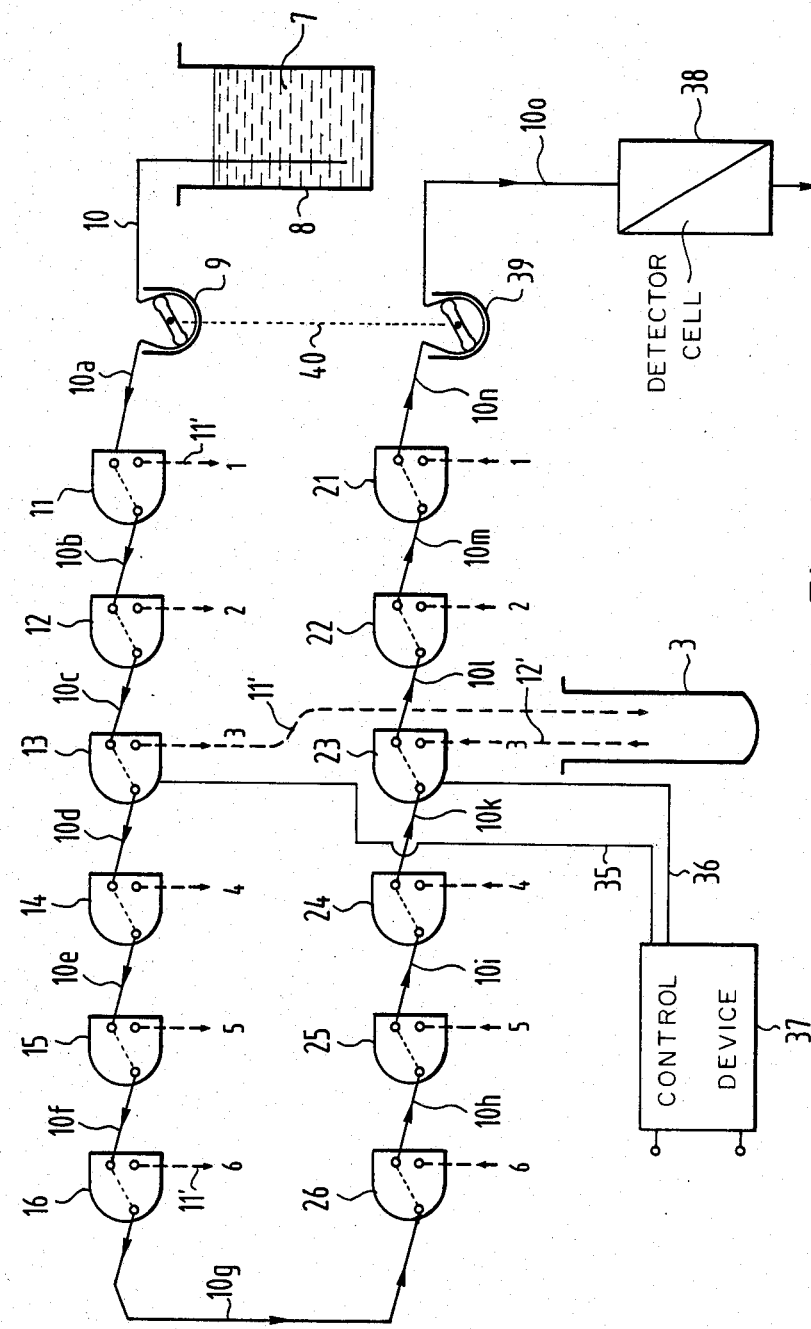

United States Patent [19]

Herzfeldt

[11] Patent Number: 4,655,094
[45] Date of Patent: Apr. 7, 1987

[54] DEVICE FOR TAKING AND MEASURING SAMPLES

[75] Inventor: Claus D. Herzfeldt, Karben, Fed. Rep. of Germany

[73] Assignee: Erweka Apparatebau GmbH, Heusenstamm, Fed. Rep. of Germany

[21] Appl. No.: 647,750

[22] Filed: Sep. 6, 1984

[51] Int. Cl.⁴ .................... G01N 1/14; G01N 1/18
[52] U.S. Cl. .................... 73/863.31; 73/864.34; 73/863.23; 73/863.01; 73/863.33
[58] Field of Search ........... 73/863.31, 863.33, 863.01, 73/864.34, 864.35, 863.23, 863.24, 863.25

[56] References Cited

U.S. PATENT DOCUMENTS

| 3,362,222 | 1/1968 | Johnson et al. | 73/863.31 X |
| 3,369,405 | 2/1968 | Galegar | 73/863.33 X |
| 3,468,166 | 9/1969 | Putnam | 73/863.33 |
| 3,524,351 | 8/1970 | Bayly et al. | 73/863.33 X |
| 3,896,673 | 7/1975 | Audoze et al. | 73/863.33 |
| 4,442,720 | 4/1984 | Apley et al. | 73/863.31 |
| 4,454,473 | 6/1984 | Brunner et al. | 73/863.31 |
| 4,462,265 | 7/1984 | Rein | 73/864.34 |
| 4,470,316 | 9/1984 | Jiskoot | 73/863.31 |

FOREIGN PATENT DOCUMENTS

| 2323603 | 1/1974 | Fed. Rep. of Germany | 73/863.31 |
| 8210451 | 2/1983 | Fed. Rep. of Germany | |
| 104231 | 8/1981 | Japan | 73/863.01 |
| 720161 | 12/1954 | United Kingdom | 73/863.31 |

Primary Examiner—Stewart J. Levy
Assistant Examiner—Tom Noland
Attorney, Agent, or Firm—Birch, Stewart, Kolasch & Birch

[57] ABSTRACT

In a device for taking and measuring samples having several testing vessels containing the samples in a testing liquid, the testing liquid is supplied to the individual testing vessels from a reservoir through a first pump and first valves which are connected to each testing vessel. From the testing vessels the samples are supplied to one or more detector cells, through second valves which are connected to the testing vessels. The second valves are arranged in a row behind each other. Between the last valve of this row and/or the detector cell(s), a second pump is provided. Thus, a serial withdrawal of samples from the individual testing vessels can be carried out with only two pumps, and the contents of the testing vessels are refilled to the nominal filling level from the reservoir at the same time.

13 Claims, 3 Drawing Figures

DEVICE FOR TAKING AND MEASURING SAMPLES

BACKGROUND OF THE INVENTION

The present invention relates to a device for taking and measuring samples, comprising, several testing vessels containing the samples in a testing liquid, at least one reservoir from which the testing liquid can be supplied to the individual testing vessels through a first pump via first valves which are connected to each testing vessel, and at least one detector cell to which the samples can be supplied from the testing vessels via second valves, which are connected to said testing vessels. In addition, the invention relates to a method for operating the device.

There is already on the market a device for taking and measuring liquid samples for analyzing purposes in pharmacy and/or chemistry (cf. DE-GM No. 82 10 451). This device consists essentially of several testing vessels in parallel. The vessels are connected with a measuring apparatus via separate lines controlled by valves, and also can be supplied with a solvent for the individual samples via a circulation system having a reservoir for the solvent. In this known device, all lines connecting the individual testing vessels with the measuring apparatus are connected in a common distributor from which only one measuring line is connected to the measuring apparatus. The purpose of this known device is to carry out an analysis with only one measuring cell, wherein the sample can be diluted or prepared in some other way, if necessary. It is also possible to discard a sample, which has already been taken, and to refill it with a pure solvent, if necessary, corresponding to existing testing rules.

Using this known device, liquid samples can be taken from the individual testing vessels in a very precise manner and be evaluated exactly in the measuring apparatus. However, for six testing vessels, for example, a total of 12 valves and 7 pumps is required. One valve is required for taking the sample and one valve is required for refilling each testing vessel. In addition, six pumps are required for taking a sample from each testing vessel and one pump is necessary for each testing vessel. The method is rather costly, particularly with respect to the large number of pumps required. The use of a distributor piece for the combination of the lines to one measuring line likewise requires a considerable amount of technical measures.

SHORT OUTLINE OF THE INVENTION

One object of the present invention is to create a device for taking and measuring samples which ensures a precise operation and at the same time a minimum expenditure. A further object of the present invention to create a method for operating such a device.

This and other objects will become clear upon reading further parts of the present specification. Thus, in a device for taking and measuring samples, the second valves are arranged in a row behind each other. Furthermore, between the end of the row of the second valves facing away from the reservoir and the detector cell, only one additional pump is provided.

In the device in accordance with the invention the second valves for the taking of the samples are arranged in a row behind each other so that only one additional pump is required for taking samples from all testing vessels.

While the device described in the DE-GM No. 82 10 451 requires n+1 pumps for n different testing vessels, the inventive device requires only two pumps, independent of the number of testing vessels. Nevertheless the inventive device ensures that impeccable analyses are carried out in a short time.

When the inventive device is in operation, a liquid sample is drawn in by means of the additional pump from only one of, for instance, six testing vessels through a filter. The sample is then supplied for the further treatment to, for example, one or several flow detector cells in order to undergo a simultaneous and/or subsequent evaluation of pH, photometric or fluorimetric. At the same time the same quantity of the pure testing liquid as the withdrawn liquid sample is added to the same testing vessel by means of the first pump, so that the level in this testing vessel is kept at a constant value.

Thus, for sampling and the refilling in the inventive device only two pumps are required which can be preferably combined to a two-channel hose pump. The individual testing vessels from which samples are taken and the filling of which is to be completed again, are selected by means of valves. Three-way magnetic valves are preferably used and they can be subsequently electrically controlled in a circulating manner. Instead of an automatic control, a manual operation can also be provided. Manual operation is particularly advantageous when the device is put into operation, which will subsequently be explained in detail.

The sampling is not necessarily combined with a refilling of the respective testing vessel. The sampling will only be directly followed by refilling when the pair of valves connected to a testing vessel is functionally connected from the first valve for the purpose of refilling and from the second valve for the purpose of taking samples.

If none of the valves are controlled, which applies for instance to a pause cycle, all valves are rinsed with a pure testing liquid and the individual filters on top of the testing vessels are left unused. The detector cell is also merely supplied with a pure testing liquid which allows a simple zero balance to be carried out. Since magnetic valves are preferably used for the valves, the zero balance can be adjusted in a simple manner by not supplying power to the magnetic valves.

The invention also provides an advantageous method for operating a device for taking and measuring samples. In this method the individual valves are first of all manually controlled so that the first pump supplies pure testing liquid from the reservoir through all valve pairs in the circulation system. Testing liquid is added to the individual reservoirs or to the detector cell, if necessary, to make a zero balance. Before manually controlling the individual valves, the filters of the individual testing vessels at the hose ends leading to the individual vessels can be cleaned with testing liquid.

The "manual control" of the individual valves one after the other for about one minute ensures that all hoses or lines are filled with liquid upstream and downstream of all valves, ensuring exact measuring results.

After a likewise manually adjusted pause the mode of operation is changed to "automatic", and the first testing vessel, any number of testing vessels or all testing vessels are charged with a sample. At the same time a recording apparatus connected with the detector cells is put into operation in order to register the measuring results. In the case of this type of operation, during switching to the following valve the corresponding testing vessel is filled with a sample.

Thus, the present invention provides a device for sequentially taking samples from testing vessels with a synchronous refilling of the testing vessels. An application of the invention may include multiple release examinations of medical substances from medical preparations. Furthermore, the inventive device, which merely requires a two-channel hose pump, can be used in connection with any detector cell.

The inventive device is particularly suited for flow analysis in connection with recording-pen registrations where samples are successively taken from the different testing vessels.

LIST OF THE DIFFERENT VIEWS OF THE FIGURES

Figure 2:
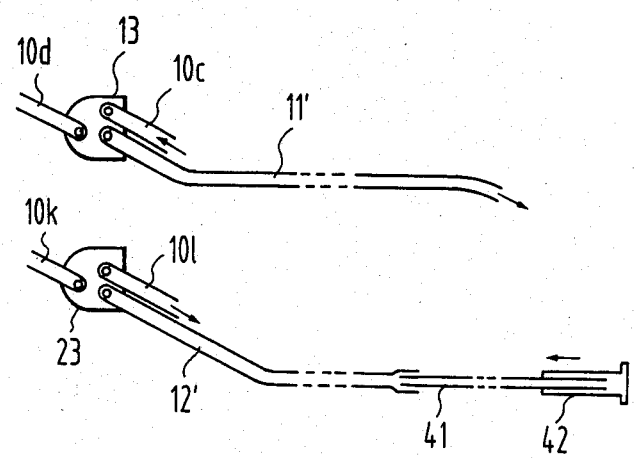
Figure 3:
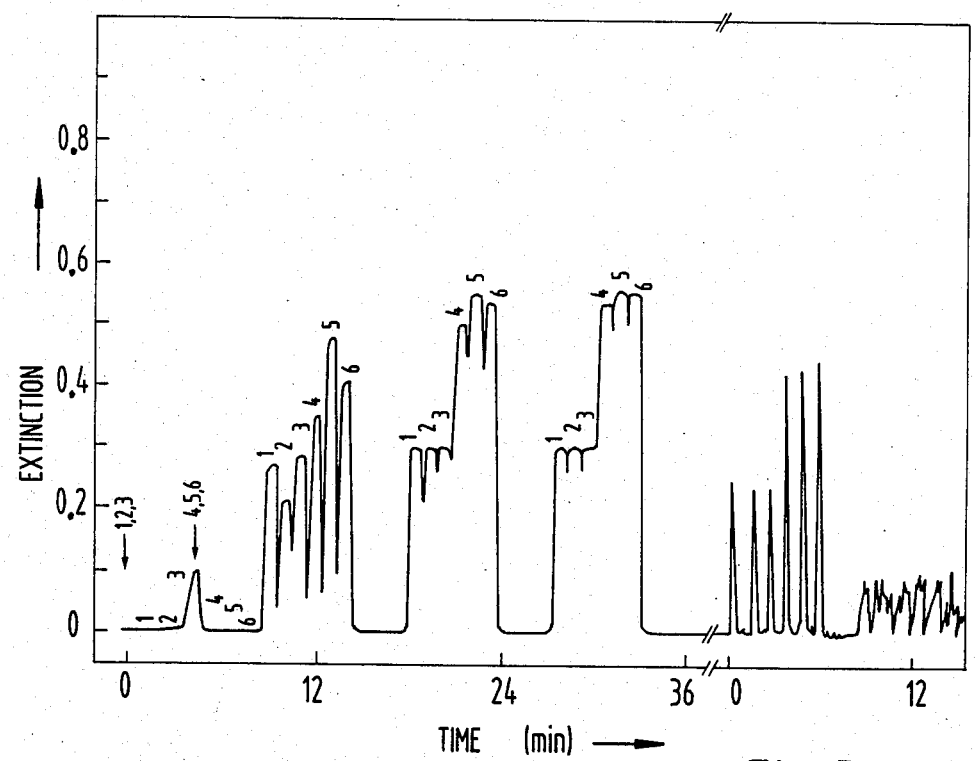

FIG. 1 shows an embodiment of the inventive device,
FIG. 2 shows a pair of magnetic valves for the inventive device, and
FIG. 3 shows the result of a spectro-photometric analysis recording-pen registration by means of the inventive device.

DETAILED ACCOUNT OF A WORKING EXAMPLE OF THE INVENTION

An embodiment of the inventive device represented in FIG. 1 shows three-way magnetic valves 11 to 16 and 21 to 26. The magnetic valves 11 to 16 serve to refill the testing vessels, while the magnetic valves 21–26 are provided for taking samples from the testing vessels.

The magnetic valves 11 to 16 and 21 to 26 are connected with each other via short hose pieces 10b to 10m, as is schematically indicated in FIG. 1. Furthermore, hoses or lines 11' lead from the magnetic valves 11 to 16 to the individual testing vessels 1 to 6. Only testing vessel 3 and line 11' which leads from the magnetic valve 13 to the testing vessel 3 are shown for the purpose of a simplified representation.

In a similar way lines 12' lead from the individual testing vessels 1 to 6 to the magnetic valves 21 to 26. Again, only the line leading to the magnetic valve 23 is shown in FIG. 1.

The magnetic valves 11 and 21 are connected to the testing vessel 1, while the magnetic valves 12 and 22 belong to the testing vessel 2 and the magnetic valves 13 to 23 to the testing vessel 3. The same applies to the magnetic valves 14 and 24 with respect to the testing vessel 4, to the magnetic valves 15 and 25 with respect to the testing vessel 5, and to the magnetic valves 16 and 26 with respect to the testing vessel 6.

The inlet of the magnetic valve 11 is connected via a hose piece 10a with the pressure side of a hose pump 9, whose suction side is immersed via a hose piece 10 into a testing liquid 7 which is contained in a reservoir 8.

When the magnetic valves 7 to 16 are not operated, the testing liquid 7 is supplied from the reservoir 8 by means of the pump 9 via the magnetic valves 11 to 16 and the magnetic valves 20 to 21 as well as the hose pieces 10, 10a to 10n to the detector cell 38.

The outlet of the magnetic valve 21 is connected via a hose piece 10n with the suction side of a second pump 39 whose pressure side is connected via a hose piece 10o to a detector cell 38 or a cuvette. When the magnetic valves 21 to 26 as well as the magnetic valves 11 to 16 are not operated, the testing liquid 7 is supplied via the valves 11 to 16 and the hose pieces 10, 10a to 10o from the reservoir to the magnetic valve 26 and then via the magnetic valves 25 to 21 and the second pump 39 to the detector cell 38 so that a zero balance can be performed in a simple manner at this detector cell.

The individual magnetic valves 11 to 16 and 21 to 26 can be controlled or manually adjusted by an electric control device 37. For the purpose of a simplified representation in FIG. 1 only the electric lines 35 and 36 between the control device 37 and the magnetic valve 13, and between the control device 37 and the magnetic valve 23 are shown. The remaining magnetic valves are of course connected to the control device 37, accordingly.

When the device is put into operation, the magnetic valves 11 to 16 are rinsed with testing liquid 7 from the reservoir 8 by means of the pump 9, which is in the pressure operation, via the hose pieces 10a to 10f. The magnetic valves 26 to 21 are likewise rinsed with testing liquid 7 from the reservoir 8 via the connection between the valves 16 and the valves 26 and via the hose pieces 10h to 10n by means of the pump 39, which is in the suction operation. This rinsing is performed at the same time, which is indicated by the dotted connection line 40 between the pumps 9 and 39. The pumps 9 and 39 can of course also be connected to the control device 37. After this rinsing the zero balance of the detector cell 38 is performed.

Then the device is switched over to an automatic control by the control device 37, which first actuates the magnetic valves 11 and 21. The magnetic valve 21 then switches over to the position leading to testing vessel 1, so that the pump 39 withdraws a sample from the testing vessel 1 and supplies said sample to the detector cell 38. At the same time the magnetic valve 11 switches over into the position leading to the line 11' so that the pump 9 supplies the testing liquid withdrawn from the reservoir 8 via the magnetic valve 11 to the testing vessel 1. In this way the same volume of testing liquid is supplied, which has been withdrawn as sample from the testing vessel 1, provided that the pumps 9 and 39 have the same efficiency, and the hoses 10, 10a to 10n, 11' and 12' have the same inner diameter.

After the magnetic valves 11 and 21 have been de-energized, the magnetic valves 12 and 22 are controlled and the operation is repeated for the testing vessel 2 in the same way as it has been explained for the testing vessel 1. The same applies to the remaining pairs of magnetic valves 13, 23; 14, 24; 15, 25 and 16, 26.

The switching of the individual pairs of magnetic valves can be performed in cycles of between 1 and 100 sec. An exact synchronization of the supply of testing liquid or samples to the magnetic valves is ensured since the pumps 9 and 39 are attached to a duplex synchronous hose pump.

FIG. 2 shows how the magnetic valves 13 and 23 are advantageously connected to their corresponding hoses. The longer end of the hose 11' serves to refill the testing vessels and the testing liquid is supplied from the magnetic valve 12 through the shorter hose piece 10c. The hose piece 10d extending from the magnetic valve 13 in FIG. 2 to the left is connected to the magnetic valve 14.

The shorter hose pieces 10l and 10k lead from the magnetic valve 23 to the magnetic valve 22 and from the magnetic valve 24, respectively. The longer hose end 12' is connected via a glass tube 41 to a reagent filter 42, which is accommodated in the testing vessel 3. In the individual magnetic valves 11 to 16 and 21 to 26 the longer end of the hose serves to refill the the testing vessels for taking samples.

Preferably, plastic hoses with an inner diameter of about 0.8 mm and an outer diameter of about 2.4 mm can be used. The glass tube 41 can have an inner diameter of 1 mm and an outer diameter of 3 mm and a length of, for instance, 150 mm. The reagent filter 42 has an inner diameter of about 3 mm.

FIG. 3 is a schematic representation of a recording-pen registration which can be obtained by the device shown in FIG. 1. The abscissa indicates the time, which is given by the paper feed velocity of the recorder. The ordinate indicates the absorbance which has been measured in the testing vessels 1 to 6 of the individual samples.

As it can be seen in FIG. 3 from the rise of the value 0 (no absorbance) to the value corresponding to vessel 1, the compensating time for the readjustment of the device is about 12 to 15 sec. This time depending largely on the dimensioning of the hoses, the detector cell and the pumping speed.

In the example shown in FIG. 3, the testing vessels 1 to 3 were charged at the same time. The testing vessels 4 to 6 were also charged at the same time, but 4 min later than the testing vessels 1 to 3. For a test evaluation this shifting of the time axis must be taken into account.

It is expedient to synchronize the charging of the testing vessels 1 to 6 with the change of the valves 11 to 16 and 21 to 26. This results in the fact that the absorbance values recorded in a series can be assigned within one cycle to a time value.

As can likewise be seen from FIG. 3, a test can be conducted by first drawing in the fluid samples to be analyzed only pure testing liquid (cf. the peak values), then pure water (no deflection to be recognized) and finally air (intermittent short deflections). Thus, an optimum cleaning of the valves 11 to 16 and 21 to 26 is obtained so that their function is not impaired by the drying up of buffer solutions or the like in the case of an extended non-use.

I claim:

1. A device for taking and measuring samples of a testing liquid, comprising:
   (a) a plurality of testing vessels;
   (b) at least one reservoir means for containing a testing liquid;
   (c) a first pump means operatively associated with said at least one reservoir and with a first row of a plurality of serially connected valve means, each of said valve means being operatively associated with respective ones of said testing vessels;
   (d) a corresponding second row of a plurality of serially connected valve means serially connected to the first row of valve means, each of said valve means in said second series operatively associated with respective ones of said testing vessels, the valve means at respectively ordered positions in each series associated with the same testing vessel;
   (e) at least one detector means for evaluating samples from the testing vessels; and
   (f) a second pump means for supplying a testing sample from said testing vessels to said detector means through at least a portion of the series of second valve means.

2. The device in accordance with claim 1, wherein each set of two valve means from different rows that are associated with the same testing vessel have both valve means therein connected to the testing vessel associated therewith and wherein each set comprises a valve pair that can be switched together.

3. The device in accordance with claim 1 wherein the valve means are three-way valves.

4. The device in accordance with claim 1, wherein a control device sequentially controls the valve means.

5. The device in accordance with claim 1, wherein the first and the second pump means are hose pumps.

6. The device in accordance with claim 5, wherein the first and the second pumps form a duplex synchronous hose pump.

7. The device in accordance with claim 1, wherein the valve means are operated manually and controlled automatically.

8. The device in accordance with claim 7, wherein the valve means are first operated manually and are then controlled automatically.

9. The device in accordance with claim 8, wherein the manual operation is performed with a duty cycle of 1 to 100 sec per valve means.

10. The device in accordance with claim 8, wherein the automatic control is performed with a duty cycle of 1 to 100 sec per valve means.

11. The device in accordance with claim 1, wherein a filter is provided in a flow path between one of said testing vessels and the one of said second valve means associated therewith.

12. The device in accordance with claim 1, wherein said at least one detector means comprises at least one detector cell having a recording device connected thereto.

13. The device in accordance with claim 1, wherein said second pump means removes a test sample from one of said testing vessels while said first pump means simultaneously supplies testing liquid to said one of said testing vessels.

* * * * *